United States Patent
You

(10) Patent No.: US 9,738,905 B2
(45) Date of Patent: Aug. 22, 2017

(54) VECTOR FOR EXPRESSING NC PROTEIN OF HIV AND METHOD FOR PRODUCING NC PROTEIN USING THE SAME

(75) Inventor: Ji Chang You, Seoul (KR)

(73) Assignees: Ji Chang You, Seoul (KR); AVIXGEN INC., Seoul (KR)

( * ) Notice: Subject to any disclaimer, the term of this patent is extended or adjusted under 35 U.S.C. 154(b) by 15 days.

(21) Appl. No.: 12/520,147

(22) PCT Filed: Dec. 20, 2007

(86) PCT No.: PCT/KR2007/006694
§ 371 (c)(1),
(2), (4) Date: Jun. 19, 2009

(87) PCT Pub. No.: WO2008/075911
PCT Pub. Date: Jun. 26, 2008

(65) Prior Publication Data
US 2010/0047865 A1    Feb. 25, 2010

(30) Foreign Application Priority Data

Dec. 20, 2006  (KR) .................. 10-2006-0131392
Dec. 20, 2006  (KR) .................. 10-2006-0131393

(51) Int. Cl.
*C12N 15/00* (2006.01)
*C12N 15/85* (2006.01)
*C07K 14/005* (2006.01)
C07K 14/16 (2006.01)
C12N 15/63 (2006.01)

(52) U.S. Cl.
CPC ............ *C12N 15/85* (2013.01); *C07K 14/005* (2013.01); *C07K 14/161* (2013.01); *C12N 15/00* (2013.01); *C12N 15/63* (2013.01); *C12N 2740/16211* (2013.01); *C12N 2740/16222* (2013.01); *C12N 2830/00* (2013.01); *C12N 2830/42* (2013.01)

(58) Field of Classification Search
CPC .................... C12N 15/00; C12N 15/63; C12N 2740/16211; C12N 2740/16222; C12N 2830/00; C12N 2830/42; C07K 14/161
See application file for complete search history.

(56) References Cited

U.S. PATENT DOCUMENTS

2008/0254008 A1* 10/2008 Dropulic et al. .......... 424/93.21

FOREIGN PATENT DOCUMENTS

KR    10/2002-0034278    *   4/2004   .......... C07K 14/435

* cited by examiner

*Primary Examiner* — Jeffrey Parkin
(74) *Attorney, Agent, or Firm* — Lucas & Mercanti, LLP

(57) ABSTRACT

The present invention relates to a vector for expressing an NC protein of HIV and a method for producing an NC protein using the same. More particularly, the present invention relates to a vector for expressing an NC protein of HIV, in which an intron sequence and an mRNA stability element in the downstream of NC gene are sequentially linked, and a method for producing an NC protein using the same. The vector for expressing an NC protein of HIV of the present invention, in which an intron sequence and an mRNA stability element in the downstream of NC gene are sequentially linked, can express a wild type NC protein in animal cells, and has an effect of improving the expression efficiency, as compared to a known art.

7 Claims, 6 Drawing Sheets

Lane 1: pCMV(-HA)
Lane 2: pCMV(-HA)NC
Lane 3: pCMV(-HA)FLAG-NC
Lane 4: pCMV(-HA)OptiNC
Lane 5: pLP1/Opti-NC+RRE

VECTOR FOR EXPRESSING NC PROTEIN OF HIV AND METHOD FOR PRODUCING NC PROTEIN USING THE SAME

CROSS-REFERENCES TO RELATED APPLICATIONS

This application is a U.S. national phase application, pursuant to 35 U.S.C. §371, of PCT/KR2007/006694, filed Dec. 20, 2007, designating the United States, which claims priority to Korean Application No. 10-2006-0131392, filed Dec. 20, 2006, and Korean Application No. 10-2006-0131393, filed Dec. 20, 2006. The entire contents of the aforementioned patent applications are incorporated herein by this reference.

TECHNICAL FIELD

The present invention relates to a vector for expressing an NC protein of HIV and a method for producing an NC protein using the same. More particularly, the present invention relates to a vector for expressing an NC protein of HIV, in which an intron sequence and an mRNA stability element in the upstream and downstream of NC gene respectively are sequentially linked, and a method for producing an NC protein using the same.

BACKGROUND ART

A nucleocapsid (hereinafter, referred to as 'NC' protein of HIV (human immunodeficiency virus) plays a structural role in virus assembly, as well as a functional role in viral life cycles, which are described as follows. First, the NC protein is involved in viral genomic encapsidation, which is attributed to two zinc finger domains consisting of a distinctive Cys-X2-Cys-X4-His-X4-Cys motif (CCHC motif). It has been known that the domain shows a high conservation in all retroviruses, and is essential for HIV RNA packaging and infectious virus production. Second, the NC protein has been known to promote the annealing of tRNA primer and strand transfer during viral reverse transcription (RT). From this, it can be seen that the NC protein plays a crucial role in viral replication. Third, the NC protein has nucleic acid chaperone activity required for viral life cycle. Further, the NC protein has been recently reported to play a specific role in the insertion of viral DNA into host chromosomes. Accordingly, it can be said that the studies on the NC protein is very important with respect to clarifying biological functions of the NC protein in HIV life cycle and the development of effective antiviral agents against crucial HIV proteins.

A prerequisite for understanding the biological functions of the NC protein in vivo is the development of effective methods for expressing the NC protein in animal cells. However, the expression of other structural proteins of HIV may be restricted in animal cells, since viral codon usage is different from that of animal cells or some of the viral genes contains what is known as an inhibitory sequence (INS). There was a problem in that the NC protein is hardly expressed in animal cells, even though the NC protein contains no INS, unlike other structural proteins of HIV. Accordingly, most studies on the NC protein have been performed by using a recombinant NC protein expressed in E. coli or by using genetic analysis.

Meanwhile, there are several examples that the level of heterologous expression is enhanced by the replacement of rare codons with those preferred by the host (codon optimization). For example, it has been reported that BPV (Bovine papillomavirus) late genes L1 and L2 are codon-optimized for the mammalian codon usage pattern, leading to increase in their expression levels in mammalian cell (Cos-1) culture, as compared to those sequence of wild type HPV (Zhou, et al., J. Virol. 73, 4972-4982, 1999). In this work, every BPV codon which occurred more than twice as frequently in BPV than in mammals (ratio of usage>2), and most codons with a usage ratio of >1.5 were conservatively replaced by the preferentially used mammalian codon. In the PCT application of WO 97/31115, WO 97/48370 and WO 98/34640 (Merck & Co., Inc.), codon optimization of HIV genes or segments thereof has been shown to result in increased protein expression and improved immunogenicity when the codon-optimized sequences are used as DNA vaccines in the host mammal for which the optimization was tailored.

The present inventors have kept the above-mentioned points in mind, and made an effort to develop a method for producing an NC protein of HIV capable of overcoming the above-described problems. We have found, however, that a wild type NC protein can not be expressed by codon-optimization alone, and that a wild type NC protein can be expressed by additionally linking an intron sequence and an mRNA stability element in the upstream and downstream of NC gene respectively and, with such RNA optimization, its expression efficiency is greatly improved, thereby completing the present invention.

DISCLOSURE

Technical Problem

Accordingly, it is an object of the present invention to provide a vector for expressing an NC protein of HIV, in which an intron sequence and an mRNA stability element in the downstream of NC gene are additionally linked, and a method for producing an NC protein using the same.

Technical Solution

In order to achieve the object, the present invention provides a vector for expressing an NC protein of HIV, in which an intron sequence and an mRNA stability element in the downstream of NC gene are additionally linked.

Further, the present invention provides a transformant transformed with the vector.

Further, the present invention provides a method for producing an NC protein of HIV using the vector.

Advantageous Effects

A vector for expressing an NC protein of HIV of the present invention, in which an intron sequence and an mRNA stability element in the downstream of NC gene are sequentially linked, can express a wild type NC protein in animal cells, and has an effect of improving the expression efficiency, as compared to the known art.

DESCRIPTION OF DRAWINGS

The above and other features of the present invention will be described in detail with reference to certain exemplary embodiments thereof illustrated by the accompanying drawings which are given hereinafter by way of illustration only, and thus are not limitative of the present invention, and wherein.

BEST MODE

Figure 1:
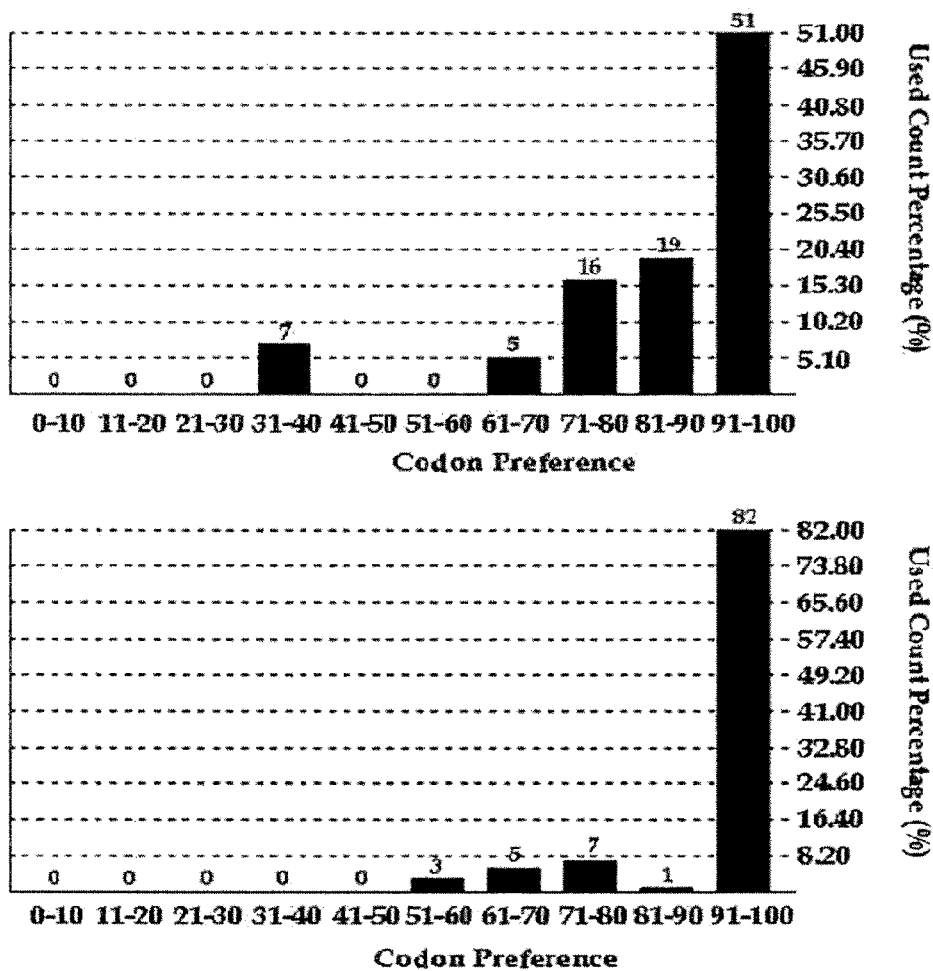
FIG. 1 is a graph showing each codon preference before and after codon optimization of an NC polynucleotide of HIV.

Hereinafter, the present invention will be described in detail with reference to examples.

However, these examples are for the illustrative purpose only, and the invention is not intended to be limited by these examples.

Example 1

Synthesis of OptiNC Polynucleotide

In order to increase the expression of an HIV-1 NC protein in mammalian cells, the RNA secondary structure, the GC content and the repetitive codon may be optimized. In the present Example, the NC codon was optimized by using the Codon Frequency Table of Upgene: A Web-Based DNA Codon Optimization Algorithm (Wentao Gao, Alexis Rzewski, Huijie Sun, Paul D. Robbins and Andrea Gambotto) and the GenScript Corporation (www.genscript.com).

First, an HIV-1 NC original base sequence was codon-optimized using a codon usage algorithm of Upgene and GenScript disclosed in the following Table 1, and each probability score was converted to the score of Upgene, which is shown in the following Table 2. With reference to Tables 1 and 2, four codon-optimized NC polynucleotide (Genscript01, Genscript02, Genscript03, Upgene) were given, and among them, the codon-optimized NC polynucleotide sequence of GenScript01 was chosen, and synthesized in GenScript. HindIII and EcoRI restriction sites were additionally inserted into the 5' and 3' ends of the synthesized codon-optimized NC polynucleotide for cloning (SEQ. ID NO. 13). GenScript01, GenScript02, and GenScript03 were represented by SEQ. ID NO. 3, SEQ. ID NO. 6, and SEQ. ID NO. 7, respectively, which were NC polynucleotides codon-optimized by using the codon usage algorithm of GenScript, and a NC polynucleotide that was codon-optimized by using the codon usage algorithm of Upgene was represented by SEQ. ID NO. 5.

TABLE 1

| Amino acid | Score | | Frequency |
|---|---|---|---|
| | DNA | Upgene | Genscript |
| ALA | GCT | 17 | 18.6 |
| | GCC | 52 | 28.5 |
| | GCA | 14 | 16 |
| | GCG | 17 | 7.6 |
| ARG | CGT | 9 | 4.7 |
| | CGC | 39 | 10.9 |
| | CGA | 7 | 6.3 |
| | CGG | 18 | 11.9 |
| | AGA | 10 | 11.5 |
| | AGG | 17 | 11.4 |
| ASN | AAT | 22 | 16.7 |
| | AAC | 78 | 19.5 |
| ASP | GAT | 32 | 22.3 |
| | GAC | 68 | 26 |
| CYS | TGT | 31 | 9.9 |
| | TGC | 69 | 12.2 |
| GLN | CAA | 12 | 11.8 |
| | CAG | 88 | 34.6 |
| GLU | GAA | 24 | 29 |
| | GAG | 76 | 40.8 |
| GLY | GGT | 10 | 10.8 |
| | GGC | 50 | 22.8 |
| | GGA | 12 | 16.3 |
| | GGG | 28 | 16.4 |
| HIS | CAT | 22 | 10.4 |
| | CAC | 78 | 14.9 |
| ILE | ATT | 18 | 15.7 |
| | ATC | 76 | 21.4 |
| | ATA | 6 | 7.1 |
| VAL | GTT | 8 | 10.9 |
| | GTC | 25 | 14.6 |
| | GTA | 7 | 7 |
| | GTG | 60 | 28.9 |
| LEU | TTA | 3 | 7.2 |
| | TTG | 4 | 12.6 |
| | CTT | 4 | 12.8 |
| | CTC | 28 | 19.4 |

TABLE 1-continued

| Amino acid | DNA | Score Upgene | Frequency Genscript |
|---|---|---|---|
| | CTA | 3 | 6.9 |
| | CTG | 58 | 40.3 |
| LYS | AAA | 18 | 24 |
| | AAG | 82 | 32.9 |
| TYR | TAT | 24 | 12 |
| | TAC | 76 | 15.6 |
| PRO | CCT | 19 | 17.3 |
| | CCC | 48 | 20 |
| | CCA | 16 | 16.7 |
| | CCG | 17 | 7 |
| PHE | TTT | 20 | 16.9 |
| | TTC | 80 | 20.4 |
| SER | TCT | 8 | 14.6 |
| | TCC | 37 | 17.4 |
| | TCA | 7 | 11.7 |
| | TCG | 20 | 4.5 |
| | AGT | 18 | 11.9 |
| | AGC | 10 | 19.4 |
| THR | ACT | 14 | 12.8 |
| | ACC | 56 | 19.2 |
| | ACA | 14 | 14.8 |
| | ACG | 16 | 6.2 |
| MET | ATG | 100 | 22.3 |
| TRP | TGG | 100 | 12.8 |
| STOP | TAA | 100 | 0.7 |
| | TAG | 100 | 0.5 |
| | TGA | 100 | 1.3 |

TABLE 2

| | Wild type NC codon | score | Optimized NC codon Upgene | score | Optimized NC codon GenScript | score |
|---|---|---|---|---|---|---|
| M | ATG | 100 | | 100 | | 100 |
| Q | CAG | 88 | | 88 | | 88 |
| R | AGA | 10 | CGC | 39 | cgg | 18 |
| G | GGC | 50 | | 50 | gga | 12 |
| N | AAT | 22 | AAC | 78 | | 78 |
| F | TTT | 20 | TTC | 80 | | 80 |
| R | AGG | 17 | CGC | 39 | agg | 17 |
| N | AAC | 78 | | 78 | | 78 |
| Q | CAA | 12 | CAG | 88 | | 88 |
| R | AGA | 10 | CGC | 39 | cga | 7 |
| K | AAG | 82 | | 82 | aaa | 18 |
| T | ACT | 14 | ACC | 56 | aca | 14 |
| V | GTT | 8 | GTG | 60 | | 60 |
| K | AAG | 82 | | 82 | | 82 |
| C | TGT | 31 | TGC | 69 | | 69 |
| F | TTC | 80 | | 80 | | 80 |
| N | AAT | 22 | AAC | 78 | aat | 22 |
| C | TGT | 31 | TGC | 69 | | 69 |
| G | GGC | 50 | | 50 | gga | 12 |
| K | AAA | 18 | AAG | 82 | | 82 |
| E | GAA | 24 | GAG | 76 | | 76 |
| G | GGG | 28 | GGC | 50 | | 50 |
| H | CAC | 78 | | 78 | | 78 |
| I | ATA | 6 | ATC | 76 | | 76 |
| A | GCC | 52 | | 52 | gct | 17 |
| K | AAA | 18 | AAG | 82 | | 82 |
| N | AAT | 22 | AAC | 78 | | 78 |
| C | TGC | 69 | | 69 | | 69 |
| R | AGG | 17 | CGC | 39 | cgg | 18 |
| A | GCC | 52 | | 52 | | 52 |
| P | CCT | 19 | CCC | 48 | | 48 |
| R | AGG | 17 | CGC | 39 | aga | 10 |
| K | AAA | 18 | AAG | 82 | | 82 |
| K | AAG | 82 | | 82 | aaa | 18 |
| G | GGC | 50 | | 50 | | 50 |
| C | TGT | 31 | TGC | 69 | | 69 |
| W | TGG | 100 | | 100 | | 100 |
| R | AGA | 10 | CGC | 39 | aga | 10 |
| C | TGT | 31 | TGC | 69 | | 69 |
| G | GGA | 12 | GGC | 50 | | 50 |
| R | AGG | 17 | CGC | 39 | aga | 10 |
| E | GAA | 24 | GAG | 76 | | 76 |
| G | GGA | 12 | GGC | 50 | | 50 |

TABLE 2-continued

|   | Wild type NC codon | | Optimized NC codon | | Optimized NC codon | |
|---|---|---|---|---|---|---|
|   |   | score | Upgene | score | GenScript | score |
| H | CAC | 78 |  | 78 |  | 78 |
| Q | CAA | 12 | CAG | 88 |  | 88 |
| M | ATG | 100 |  | 100 |  | 100 |
| K | AAA | 18 | AAG | 82 |  | 82 |
| D | GAT | 68 |  | 68 |  | 68 |
| C | TGC | 69 |  | 69 |  | 69 |
| T | ACT | 14 | ACC | 56 | act | 14 |
| E | GAG | 76 |  | 76 |  | 76 |
| R | AGA | 10 | CGC | 39 |  | 39 |
| Q | CAG | 88 |  | 88 |  | 88 |
| A | GCT | 17 | GCC | 52 | gca | 14 |
| N | AAT | 22 | AAC | 78 |  | 78 |
| STOP | TGA | 100 |  | 100 |  | 100 |
|   | Total | 2286 |  | 3706 |  | 3106 |

Each codon preference before (A in FIG. 1) and after (B in FIG. 1) codon optimization of the above synthesized HIV NC polynucleotide (GenScripte01) is shown in FIG. 1. FIG. 1 shows codon percentage used in wild type NC and codon-optimized NC sequences according to codon preference used in mammalian cells.

Example 2

Construction of Vector for Expressing NC Protein of HIV 2-1. Construction of pCMV(-HA)NC/RRE Vector A vector for expressing an NC protein of HIV, in which an SV40 SD/SA intron sequence, an HIV NC gene and RRE are sequentially linked, was constructed.

Figure 2:
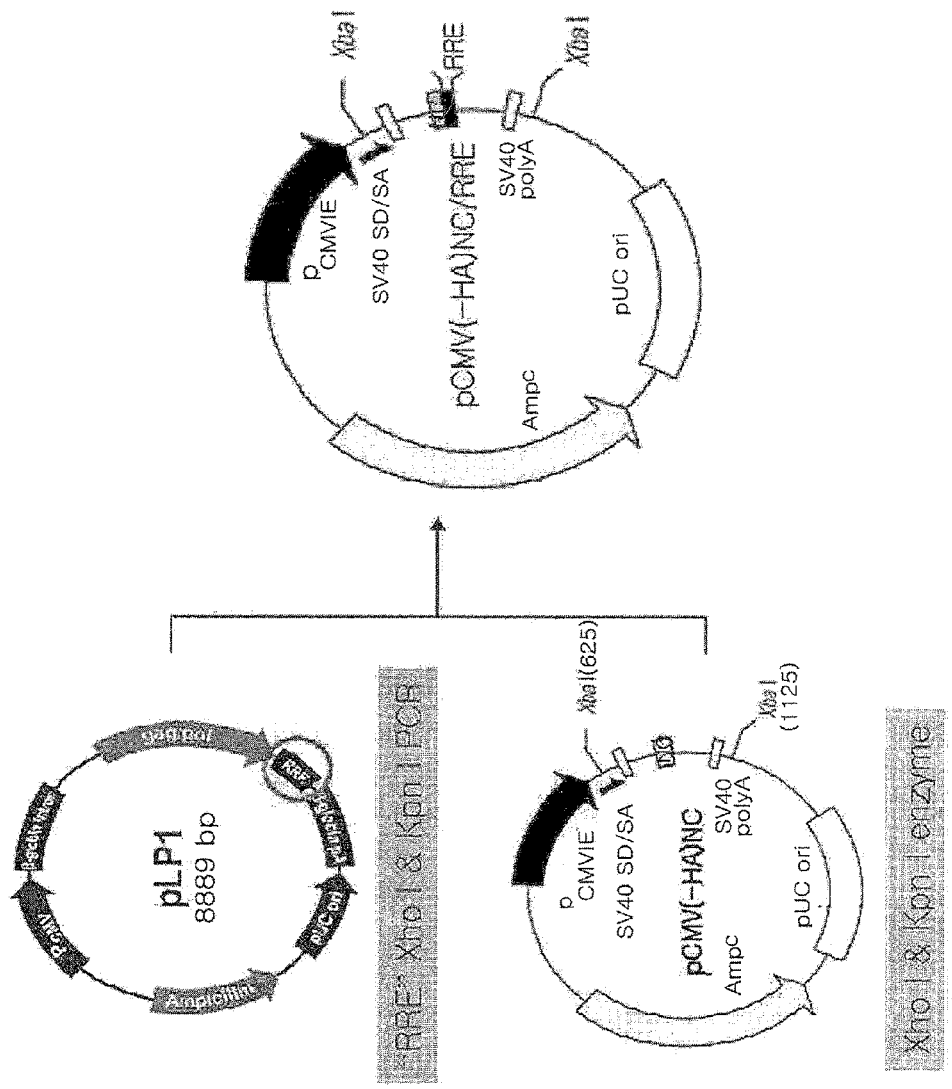
FIG. 2 is a diagram showing the production process of the vector for expressing an NC protein of HIV, pCMV(-HA) NC/RRE according to the present invention.

The vector construction process is illustrated in FIG. 2. First, in order to amplify RRE, PCR was performed using a pLP1 vector (Invitrogen) as a template and using a forward primer (5'GCGCTCGAGAGGAGCTTTGTTCCTTGGG-3' SEQ. ID NO. 1) and a reverse primer (5'TAAGGTACCA-GGAGCTGTTGATCCTTTA-3' SEQ. ID NO. 2). The forward and reverse primer was designed as to have XhoI and KpnI restriction site, respectively. The amplified RRE was treated with XhoI and KpnI. The fragment treated with the restriction enzymes was cloned with a pCMV(-HA)NC vector (Korea Patent No. 553154) that had been treated with XhoI and KpnI, and the resultant was designated as pCMV(-HA)NC/RRE.

2-2. Construction of pCMV(-HA)/OptiNC Vector

A vector for expressing an NC protein of HIV, in which an SV40 SD/SA intron sequence and a codon-optimized HIV NC (Optimized HIV NC) gene are sequentially linked, was constructed.

Figure 3:
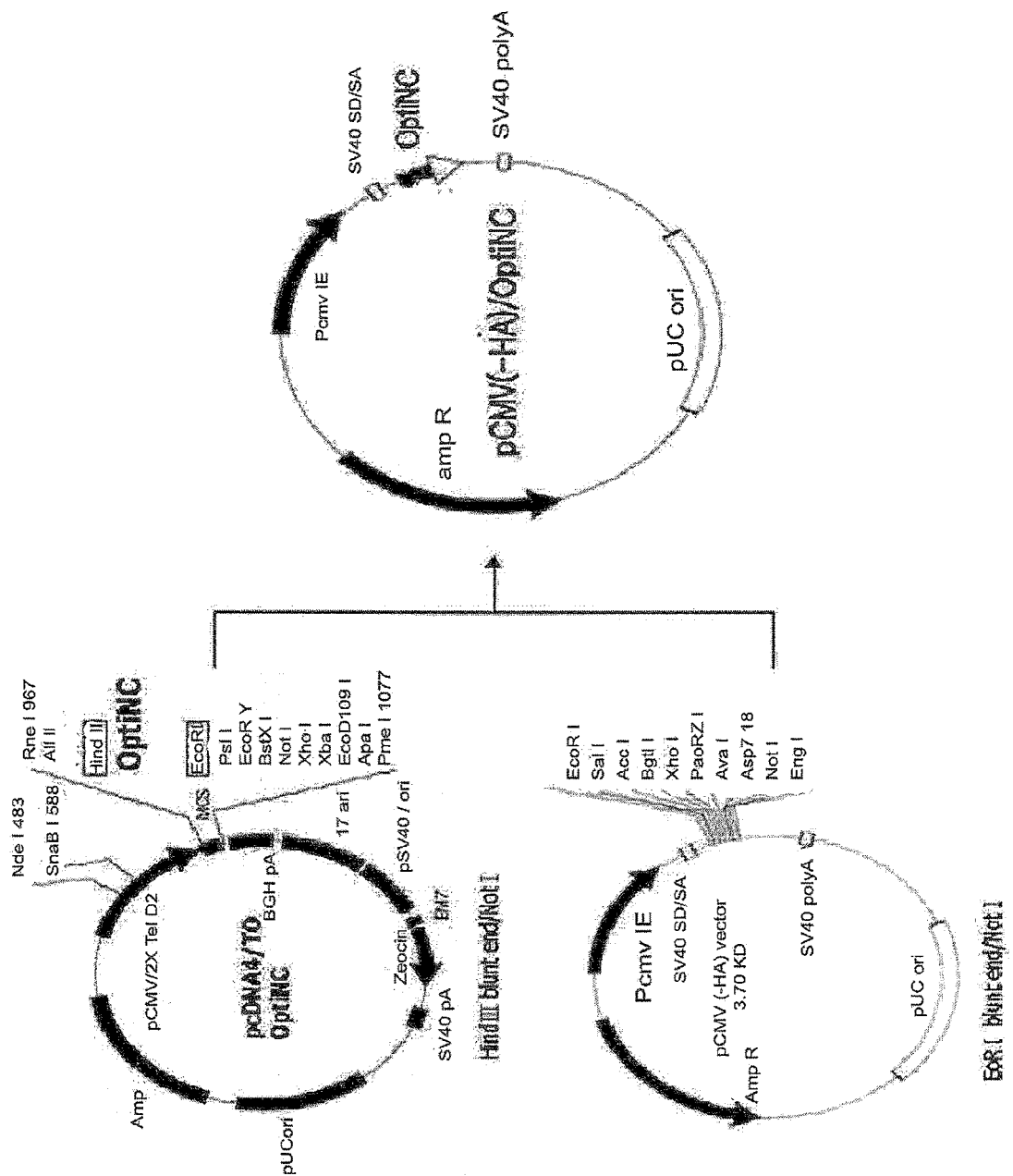
FIG. 3 is a diagram showing the production process of the vector for expressing an NC protein of HIV, pCMV(-HA)/OptiNC according to the present invention.

The vector construction process is illustrated in FIG. 3. The OptiNC gene (SEQ. ID NO. 5) synthesized in Example 1 was treated with EcoRI/HindIII restriction enzymes, and then the fragment treated with the restriction enzymes was cloned with a pUC57 vector (GenScript) that had been treated with EcoRI/HindIII, and the resultant was designated as pUC57/OptiNC. The pUC57/OptiNC and pcDNA4/TO (Invitrogen) were digested with HindIII and EcoRI, and then ligated to obtain pcDNA4/TO/OpicNC. The pcDNA4/TO/OptiNC was treated with HindIII and NotI, and then the digested DNA was treated with the Klenow fragment. The pCMV(-HA) vector (Clontech Laboratories, Inc.) was treated with EcoRI and NotI, and then the digested DNA was treated with the Klenow fragment. The two fragments treated with the Klenow fragment were ligated, and the resultant was designated as pCMV(-HA)/OptiNC.

2-3. Construction of pCMV(-HA)OptiNC/RRE Vector

Figure 4:
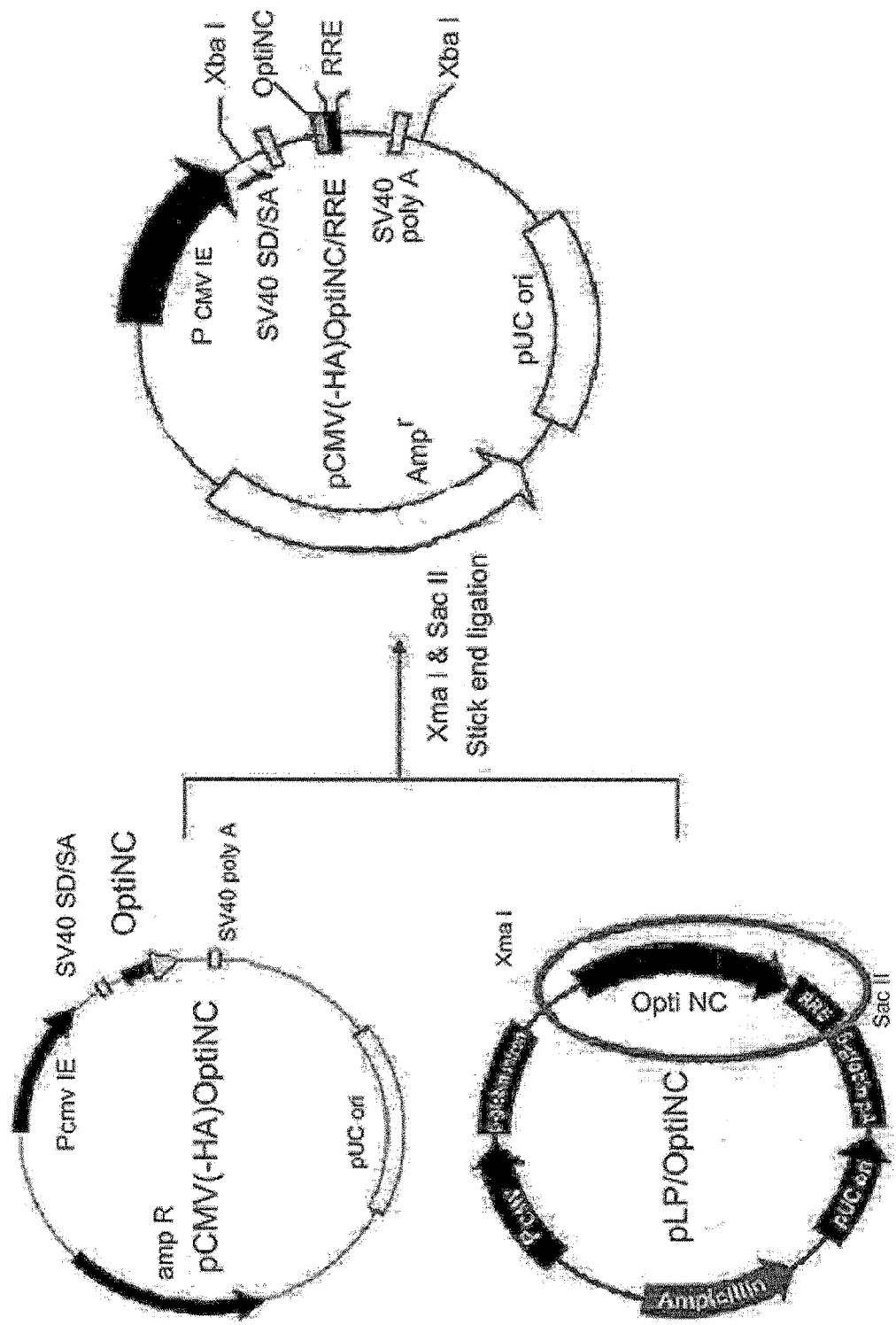
FIG. 4 is a diagram showing the production process of the vector for expressing an NC protein of HIV, pCMV(-HA) OptiNC/RRE according to the present invention.

A vector for expressing an NC protein of HIV, in which an SV40 SD/SA intron sequence, a codon-optimized HIV NC gene, and RRE are sequentially linked, was constructed. The vector construction process is illustrated in FIG. 4.

First, a pLP/OptiNC vector was manufactured as described below: A pLP1 vector (Invitrogen) was treated with PmlI/AvrII/BspEI, and a GAG-POL gene was cut off. The pCMV(-HA)/OptiNC vector manufactured in Example 2-2 was treated with XmaI/EcoRI to obtain an OptiNC gene. The pLP1 vector and the obtained OptiNC gene were treated with the Klenow fragment for blunt end ligation, and the resultant was designated as a pLPOptiNC/RRE vector.

The obtained pLPOptiNC/RRE vector was treated with XmaI/SacII to give a gene fragment, in which OptiNC and RRE were linked, and then the obtained fragment was cloned with the pCMV(-HA)/OptiNC vector that had been treated with XmaI/SacII. The resultant was designated as pCMV(-HA)OptiNC/RRE.

2-4. Construction of pCMV(-HA) FLAG NC Vector

A pCMV(-HA) FLAG NC vector was manufactured as follows: an NC gene fragment, which was obtained by treating pJC1 [HIV Nucleocapsid Protein; Expression in *E. coli*, Purification and Characterization. *J. Biol. Chem.*, 268, 16519-16527, 1993] with restriction enzymes BglI and PstI, was inserted into a pCMV Tag 2B vector (Stratagene, USA) treated with BamH1 and PstI to manufacture a pCMV FLAG NC vector. Then, the pCMV (-HA) vector and FLAG NC gene fragment, which was obtained by sequentially treating the pCMV FLAG NC vector with restriction enzymes, SalI, Klenow fragment, and Xho1, were ligated to manufacture a pCMV (-HA) FLAG NC vector.

Example 3

Expression of NC Protein of HIV 3-1. Cell Transformation 293T cells were cultured in DMEM (Dulbecco modified Eagle's medium) containing 1% streptomycin/penicillin and 10% (v/v) fetal bovine serum (FBS). One day before transformation, the cultured cells were inoculated in a 12-well plate at a density of $1 \times 10^6$ cells per well, and cultured to show about 60 to 80% confluency. Each 1 μg of pCMV(-HA)NC/RRE, pCMV(-HA)/OptiNC and pCMV(-HA)OptiNC/RRE manufactured in Example 2 was taken, and each was mixed with 2 μl of jetPEI reagent (Polyplus-transfection Inc.), and reacted in 200 μl of serum-free media at room temperature for 20 minutes. Subsequently, the wells containing cells to be transformed were divided into three groups, and then the culture media were exchanged with 1 ml of serum-free media. The mixed solution of the vector and jetPEI reagent was added to each cell in the serum-free media, and further cultured in a $CO_2$ incubator for 4 hours. After culturing, the culture media were exchanged with DMEM media containing 10% (v/v) FBS, and then cultured for additional 2 days. Then, the cells were collected.

3-2. Western Blot for Confirmation of NC Protein Expression

In order to confirm the expression of NC protein in the transformed cells, a western blot was performed. First, in order to extract the protein from the obtained cells, each cell was dissolved with a lysis solution (50 mM Tris-HCl (pH 7.4), 150 mM NaCl, 1 mM EDTA, 1% TyitonX-100, 1% sodium deoxycholate, 1% SDS, protease inhibitor cocktail) and then centrifuged at 15,000 rpm for 20 minutes. The supernatant was collected, and then 15% SDS-PAGE was performed. Then, a western blot was performed using anti-NC monoclonal antibodies, and the expression level were converted to numerical values (FIG. 5).

Figure 5:
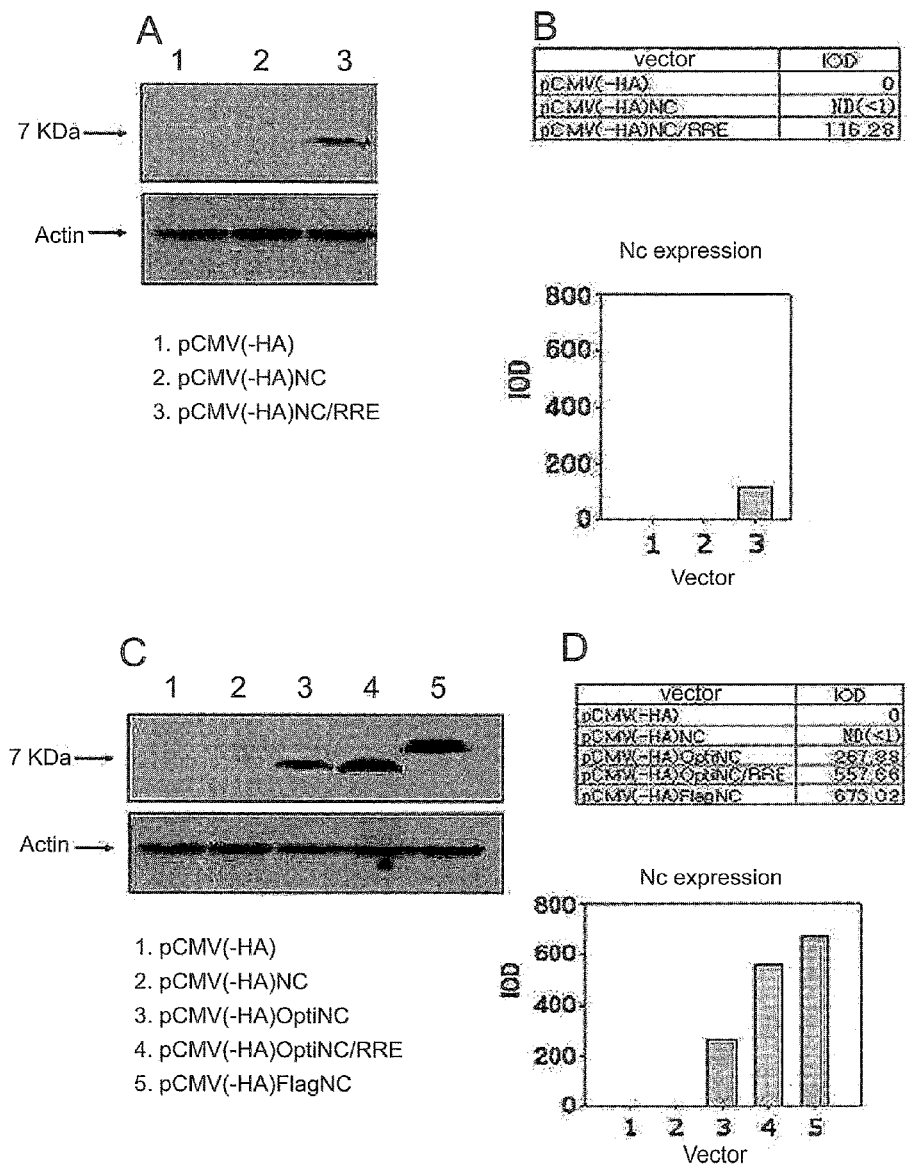
FIG. 5 show the result of western blot (A and C) to compare expression level of the NC protein in cells transformed with the vector for expressing an NC protein of HIV according to the present invention, and diagrams (B and D) showing numerical values of the quantified expression level.

Consequently, as shown in FIG. 5, the expression level of 116.28 IOD, 267.88 IOD, and 557.66 IOD were shown in the cells transformed with the pCMV(-HA)NC/RRE vector containing an mRNA stability element, cells transformed with the pCMV(-HA)/OptiNC vector containing a sequence coding for the optimized NC protein, and cells transformed with the pCMV(-HA)OptiNC/RRE vector simultaneously containing sequences coding for an mRNA stability element and the optimized NC protein, respectively, which indicates that the expression level was significantly improved in pCMV(-HA)OptiNC containing the codon-optimized NC gene, as compared to pCMV(-HA)NC containing the wild type NC gene (lanes 2 and 3 in FIG. 5C). From this, it can be seen that the NC protein can be expressed with a high yield, when the wild type NC gene was substituted with the codon-optimized NC polynucleotide. In addition, it was found that the expression was significantly improved in pCMV(-HA)OptiNC/RRE containing the mRNA stability element, as compared to pCMV(-HA)NC, in which the RRE sequence was not inserted into the downstream of NC gene (lanes 2 and 4 in FIG. 5C). From this, it can be seen that RRE affects the expression of NC protein, which indicates that the expression of NC protein can be increased by linking the combination of OptiNC and RRE sequence to the downstream of intron sequence.

Moreover, it can be seen that the wild type NC protein can be expressed by using the vector of the present invention, similar to pCMV(-HA)FlagNC, in which the FLAG gene is further linked to the upstream of NC polynucleotide.

Example 4

Production of NC Protein Using pLPOptiNC/RRE Vector

Figure 6:
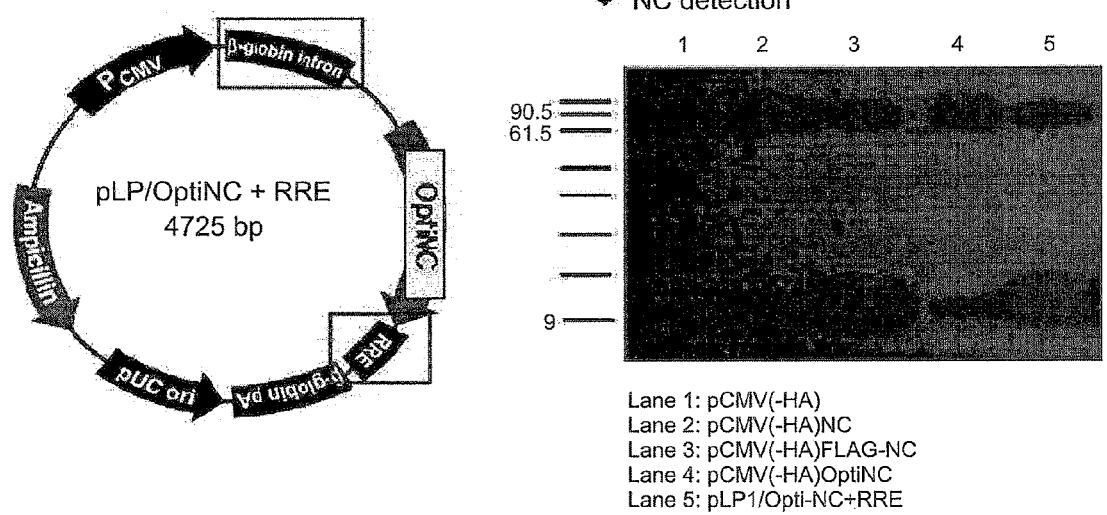
FIG. 6 is the result of western blot, which determines expression level of the NC protein by the vector having a β-globin intron among the vectors for expressing an NC protein of HIV.

In order to confirm the effect of improving the expression efficiency of NC protein in the case of using a β-globin intron other than the SV40 19s mRNA intron sequence and modified SV40 16S mRNA intron sequence as an intron sequence, 293T cells were transformed with the pLPOptiNC/RRE vector manufactured in Example 2-3 in the same manner as Example 3-1, and then cultured. Subsequently, in order to confirm the expression of NC protein, a western blot was performed in the same manner as Example 3-2.
Consequently, as shown in FIG. 6, it was found that in the case of using the β-globin intron sequence, the wild type NC protein can be expressed, and the expression level of NC protein is similar to those in pCMV(-HA)FlagNC, in which the FLAG gene is further linked to the upstream of NC polynucleotide (lanes 3 and 5 in FIG. 6).

MODE FOR INVENTION

Hereinafter, the present invention will be described in detail.
The production of the nucleocapsid (NC) protein of HIV is very important to develop effective antiviral agents, but it is still hard to express the NC protein of HIV in animal cells. The present inventors have conducted studies in order to improve the problem, and we found that the expression of the NC protein of HIV is significantly improved by using a vector for expressing an NC protein of HIV, in which an intron sequence and an mRNA stability element in the downstream of NC gene are additionally linked.

Accordingly, the present invention provides a vector for expressing an NC protein of HIV, in which an intron sequence, an HIV NC gene and an mRNA stability element are sequentially linked.

More specifically, the present invention provides a vector for expressing an NC protein of HIV, in which a) any one sequence selected from the group consisting of an SV40 19s mRNA intron sequence, a modified SV40 16S mRNA intron sequence and β-globin intron sequence, b) an NC gene of HIV, and c) an mRNA stability element are sequentially linked.

The term "NC protein of HIV" means a nucleocapsid protein of HIV (human immunodeficiency virus), which causes AIDS (acquired immunodeficiency syndrome), and the protein strongly binds to the viral genome RNA to form a ribonucleoprotein core complex. An NC protein sequence of HIV expressed in one embodiment of the present invention is derived from ARV2/SF, and is disclosed as 380th to 434th amino acid sequences of Genebank Accession No. P03349. On the other hand, an NC gene sequence used in one embodiment of the present invention is derived from a pJC1 vector [HIV Nucleocapsid Protein; Expression in *E. coli*, Purification and Characterization, *J. Biol. Chem.* 268, 16519-16527, 1993].

The term "expression" as used herein means production of proteins or nucleic acids in cells.

The term "expression vector" as used herein refers to a vector capable of expressing a target protein or target RNA in an adequate host cell, and refers to a genetic construct containing essential regulatory elements to which a gene insert is operably linked in such a manner as to be expressed.

In the expression vector of the present invention, a promoter is operably linked to a structural gene, in which an intron sequence, an NC gene of HIV and an mRNA stability element of the present invention are sequentially linked, for the expression of the NC protein of HIV. The "promoter" means a DNA sequence regulating the expression of nucleic acid sequence operably linked in a specific host cell, and either a constitutive promoter which continually induces expression of target gene at all times or an inducible promoter which induces the same at particular position and time may be used.

The term "operably linked" as used herein refers to a functional linkage between a nucleic acid expression control sequence and a nucleic acid sequence coding for a target protein or RNA in such a manner as to allow general functions. For example, a promoter may be operably linked to a nucleic acid coding for a protein or RNA and affect the expression of the coding nucleic acid sequence. The operable linkage to a recombinant vector may be prepared using a genetic recombination technique well known in the art, and site-specific DNA cleavage and ligation may be easily achieved using restriction enzymes generally known in the art.

Examples of the vector of the present invention include a plasmid vector, a cosmid vector, a bacteriophage vector and a viral vector, but are not limited thereto. The preferred expression vector includes regulatory elements for gene expression such as a promoter, operator, an initiation codon, a stop codon, a polyadenylation signal, and an enhancer, and a variety of vectors can be prepared according to the purpose. The vector of the present invention may be preferably a pCMV(-HA)NC/RRE vector or a pCMV(-HA) OptiNC/RRE vector described in FIG. 2 or FIG. 4.

In the present invention, the intron sequence known in the related art can be used, for example, an SV40 19s mRNA intron sequence, a modified SV40 16S mRNA intron sequence and a β-globin intron sequence. An SV40 19s mRNA intron sequence represented by SEQ. ID NO. 8, a modified SV40 16S mRNA intron sequence represented by SEQ. ID NO. 9 and a β-globin intron sequence represented by SEQ. ID NO. 10 can be preferably used.

The intron sequence used in one embodiment of the present invention is derived from an intron sequence (SV40 splice donor/splice acceptor; hereinafter, referred to as 'SV40 SD/SA') of a pCMV-HA vector (Clontech Laboratories, Inc.). Sequence 672 through 702 of the vector is the SV40 19S mRNA intron sequence, and sequence 672 through 768 of the vector is the modified SV40 16S mRNA intron sequence.

Meanwhile, any NC gene of HIV coding for the NC protein of HIV can be used as long as it can express an NC protein of HIV having an amino acid sequence of SEQ. ID NO. 4, and may have any nucleotide sequences selected from the group consisting of SEQ. ID NO. 3, SEQ. ID NO. 5, SEQ. ID NO. 6 and SEQ. ID NO. 7 or an NC gene of wild type HIV. Preferably the HIV NC gene of the present invention is codon-optimized to be highly expressed in mammalian cells. More specifically, the gene has any nucleotide sequence selected from the group consisting of SEQ. ID NO. 3, SEQ. ID NO. 5, SEQ. ID NO. 6 and SEQ. ID NO. 7.

The term "codon optimization" as used herein refers to coding regions or genes of nucleic acid molecules for transformation of various hosts, and also refers to the alteration of coding regions of the nucleic acid molecules or codons in the gene to reflect the typical codon usage of the host organism without altering the polypeptide encoded by the DNA. Within the context of the present invention, genes and DNA coding regions are codon-optimized for optimal expression in mammalian cells using Tables 1 and 2.

Codon optimization synthesizes all (or portions) of the DNA to remove any destabilizing sequences or regions of secondary structure that would be present in the transcribed mRNA, or synthesizes all (or portions) of the DNA to alter the base composition to those more preferable in the desired host cell.

In the present invention, the NC codon is optimized by using the Codon Frequency Table of Upgene: A Web-Based DNA Codon Optimization Algorithm (Wentao Gao, Alexis Rzewski, Huijie Sun, Paul D. Robbins and Andrea Gambotto) and the GenScript Corporation (www.genscript.com), thereby obtaining HIV-NC polynucleotide sequences represented by SEQ. ID NO. 3, SEQ. ID NO. 5, SEQ. ID NO. 6 and SEQ. ID NO. 7, which are codon-optimized to be highly expressed in mammalian cells (see Example 1).

The term "mRNA stability element" was used herein refers to a stability element that binds to 3' end of mRNA to increase stability, and may be preferably any one selected from the group consisting of RRE (Rev response element), WPRE (woodchuck post-transcriptional regulatory element), β-actin 3'-UTR (untranslated regions) and RSV stability element (Rous sarcoma virus stability element).

RRE among the mRNA stability elements refers to a Rev responsive element (RRE). RRE is a cis-acting element present in the env gene of HIV-1 RNA and directly binds to a Rev protein. WPRE refers to a post-transcriptional regulatory element (PRE) derived from woodchuck hepatitis virus, and refers to a virus sequence that acts as cis at the post-transcriptional level and regulates the export from nucleus to cytoplasm to increase the accumulation of gene transcripts in cytoplasm. Both the β-actin 3'-UTR and the RSV stability element are sequences that regulate the transportation from nucleus to cytoplasm or prevent degradation to increase the accumulation of gene transcripts in cytoplasm.

In one embodiment of the present invention, the RRE base sequence is used as the mRNA stability element, and the RRE is derived from the HIV HXB2 strain and known as GenBank Accession No. K03455. In the sequence, sequence 7769 through 8002 corresponding to the RRE is represented by SEQ. ID NO. 11. Meanwhile, a sequence derived from the WHV8 strain of woodchuck hepatitis virus [*Journal of Virology* April 1999, p. 2886-2892] is used as WPRE, and in the described sequence, sequence 1093 through 1684 corresponding to the WPRE is represented by SEQ. ID NO. 12. Further, as the β-actin 3'-UTR and RSV stability element, the sequences described in the following publications may be used [The 3'-end of the human beta-actin gene enhances activity of the beta-actin expression vector system: construction of improved vector., *Journal of Biochemical & Biophysical Methods*. 36(1):63-72, 1997; A 3'UTR sequence stabilizes termination codons in the unspliced RNA of Rous sarcoma virus, RNA-A Publication of the RNA Society, 12(1):102-10, 2006.].

Further, in one embodiment of the present invention, a vector for expressing an NC protein of HIV, in which an SV40 SD/SA intron sequence, an HIV NC gene and RRE are sequentially linked, is constructed, and it was confirmed that the NC protein was highly expressed in a transformant transformed with the vector (see Example 3-2).

The standard recombinant DNA and molecular cloning techniques used in the present invention are well known in the related art, and described in the following publications [Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)].

Further, the present invention provides a cell transformed with the vector for expressing an NC protein of HIV.

The transfection of vector for expressing an NC protein of HIV can be performed using conventional transfection methods such as DEAE-dextran mediated transfection, calcium phosphate transfection, microinjection, DNA-containing liposome, and lipofectamine-DNA complex, as known in the related art. A suitable standard technique can be adopted depending on host cells [Molecular Cloning, Cold Spring Harbor, N.Y., Cold Spring Harbor Laboratory Press (1989)].

The cell transformed with the vector of the present invention is not specifically limited, but preferably COS-7, 293T, HEK293T, CHO and HeLa cells, and more preferably COS-7 and 293T cells.

Further, the present invention provides a method for producing an NC protein of HIV, comprising the step of culturing the cells transformed with the vector.

In one embodiment of the present invention, 293T cells transformed with the vector for expressing an NC protein of HIV of the present invention were cultured using a known method in the art. As a result, a wild type NC protein of HIV was confirmed to be expressed (see Example 3-2).

The protein expressed in the transformant may be purified by various common methods, which may be used separately or in combination, for example, salting out (e.g., ammonium sulfate precipitation, sodium phosphate precipitation, etc.), solvent precipitation (e.g., protein fraction precipitation using acetone, ethanol, etc.), dialysis, gel filtration, chromatographic methods such as ion exchange chromatography and reverse phase chromatography, and ultrafiltration [Maniatis, et al., Molecular Cloning: A Laboratory Manual, Cold Spring Harbor Laboratory, Cold Spring Harbor, N.Y. (1982); Sambrook, et al., Molecular Cloning: A Laboratory Manual, 2d Ed., Cold Spring Harbor Laboratory Press (1989); Deutscher, M., Guide to Protein Purification Methods Enzymology, vol. 182. Academic Press Inc., San Diego, Calif. (1990)].

The present invention further provides a polynucleotide coding for the NC protein of HIV, which is codon-optimized to be highly expressed in mammalian cells. More particularly, the polynucleotide of the present invention consists of any one base sequence selected from the group consisting of SEQ. ID NO. 3, SEQ. ID NO. 5, SEQ. ID NO. 6 and SEQ. ID NO. 7.

INDUSTRIAL APPLICABILITY

As described above, a vector for expressing an NC protein of HIV, in which an intron sequence and an mRNA stability element in the downstream of NC gene are sequentially linked, can express a wild type NC protein in animal cells, and has an effect of improving the expression efficiency, as compared to the known art.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. A vector for expressing a nucleocapsid (NC) protein of Human Immunodeficiency Virus (HIV), comprising
   a) any one sequence selected from the group consisting of an SV40 19s mRNA intron sequence of SEQ ID NO:8, a modified SV40 16S mRNA intron sequence of SEQ ID NO:9 and a β-globin intron sequence of SEQ ID NO: 10,
   b) a gene encoding for an HIV NC protein of SEQ. ID NO. 4, selected from the group consisting of SEQ ID NO:3, 5, 6 AND 7, and
   c) an mRNA stability element
   wherein the genes of a)-c) are sequentially linked.

2. The vector for expressing an NC protein of HIV according to claim 1, wherein the mRNA stability element is any one selected from the group consisting of RRE (Rev response element), WPRE (woodchuck post-transcriptional regulatory element), .beta.-actin 3'-UTR (untranslated regions) and RSV stability element (Rous sarcoma virus stability element).

3. The vector according to claim 1, wherein the vector for expressing an NC protein of HIV has a cleavage map disclosed in FIG. 2 or FIG. 4.

4. An isolated cell transformed with the vector of any one of claim 2, or 3.

5. The transformed cell according to claim 4, wherein the cell is a COS-7 or 293T cell.

6. A method for producing an NC protein of HIV, comprising the step of culturing the transformed cell of claim 4.

7. A codon-optimized HIV NC polynucleotide for high expression in mammalian cells, comprising a nucleotide sequence represented by any one selected from the group consisting of SEQ. ID NO. 3, SEQ. ID NO. 5, SEQ. ID NO. 6 and SEQ. ID NO. 7.

* * * * *

```
                         SEQUENCE LISTING

<160> NUMBER OF SEQ ID NOS: 13

<210> SEQ ID NO 1
<211> LENGTH: 28
<212> TYPE: DNA
<213> ORGANISM: Artificial Sequence
<220> FEATURE:
<223> OTHER INFORMATION: 5' sense primer for amplification of RRE

<400> SEQUENCE: 1
gcgctcgaga ggagctttgt tccttggg                                          28

<210> SEQ ID NO 2
<211> LENGTH: 28
<212> TYPE: DNA
<213> ORGANISM: Artificial Sequence
<220> FEATURE:
<223> OTHER INFORMATION: 3' anti-sense primer for amplification of RRE

<400> SEQUENCE: 2
taaggtacca ggagctgttg atccttta                                          28

<210> SEQ ID NO 3
<211> LENGTH: 168
<212> TYPE: DNA
<213> ORGANISM: Artificial Sequence
<220> FEATURE:
<223> OTHER INFORMATION: Codon-optimized HIV NC
      poly-nucleotide(GenScript)

<400> SEQUENCE: 3
atgcagcggg gaaacttcag gaaccagcga aaaactgtga agtgcttcaa ttgcggaaag       60
gagggccaca tcgctaagaa ctgccgggcc cccagaaaga aaggctgctg gagatgcggc      120
agagagggcc accagatgaa ggactgcact gagcggcagg caaactga                   168

<210> SEQ ID NO 4
<211> LENGTH: 55
<212> TYPE: PRT
<213> ORGANISM: Artificial Sequence
<220> FEATURE:
<223> OTHER INFORMATION: Codon-optimized HIV NC poly-peptide(GeneScript)

<400> SEQUENCE: 4

Met Gln Arg Gly Asn Phe Arg Asn Gln Arg Lys Thr Val Lys Cys Phe
1               5                   10                  15
```

Asn Cys Gly Lys Glu Gly His Ile Ala Lys Asn Cys Arg Ala Pro Arg
             20                  25                  30

Lys Lys Gly Cys Trp Arg Cys Gly Arg Glu Gly His Gln Met Lys Asp
         35                  40                  45

Cys Thr Glu Arg Gln Ala Asn
         50              55

<210> SEQ ID NO 5
<211> LENGTH: 168
<212> TYPE: DNA
<213> ORGANISM: Artificial Sequence
<220> FEATURE:
<223> OTHER INFORMATION: Codon-optimized HIV NC poly-nucleotide(Upgene)

<400> SEQUENCE: 5
atgcagcgcg gcaacttccg caaccagcgc aagaccgtga agtgcttcaa ctgcggcaag      60
gagggccaca tcgccaagaa ctgccgcgcc cccgcaaga agggctgctg gcgctgcggc     120
cgcgagggcc accagatgaa ggactgcacc gagcgccagg ccaactga                 168

<210> SEQ ID NO 6
<211> LENGTH: 168
<212> TYPE: DNA
<213> ORGANISM: Artificial Sequence
<220> FEATURE:
<223> OTHER INFORMATION: Codon-optimized HIV NC poly-nucleotide
      (Genscript02)

<400> SEQUENCE: 6
atgcagcggg gaaacttcag gaaccagcgg aaaactgtga agtgcttcaa ttgcggaaag      60
gagggccaca tcgctaagaa ctgccgcgcc cccagaaaga aaggctgctg gagatgcggc    120
agagagggcc accagatgaa ggactgcaca gagcgccagg caaactga                 168

<210> SEQ ID NO 7
<211> LENGTH: 168
<212> TYPE: DNA
<213> ORGANISM: Artificial Sequence
<220> FEATURE:
<223> OTHER INFORMATION: Codon-optimized HIV NC poly-nucleotide
      (Genscript03)

<400> SEQUENCE: 7
atgcagcggg gaaacttcag gaaccagagg aaaactgtga agtgcttcaa ttgcggaaag      60
gagggccaca tcgctaagaa ctgcagggcc cccagaaaga aaggctgctg gagatgcggc    120
agagagggcc accagatgaa ggactgcacg gagaggcagg caaactga                 168

<210> SEQ ID NO 8
<211> LENGTH: 30
<212> TYPE: DNA
<213> ORGANISM: Artificial Sequence
<220> FEATURE:
<223> OTHER INFORMATION: SV40 late 19S mRNA intron

<400> SEQUENCE: 8
gtaagtttag tcttttgtc ttttatttca                                        30

<210> SEQ ID NO 9
<211> LENGTH: 97
<212> TYPE: DNA
<213> ORGANISM: Artificial Sequence
<220> FEATURE:
<223> OTHER INFORMATION: Modified SV40 late 16S mRNA intron

<400> SEQUENCE: 9

```
gtaagtttag tcttttgtc ttttatttca ggtcccggat ccggtggtgg tgcaaatcaa    60
agaactgctc ctcagtggat gttgccttta cttctag                            97
```

<210> SEQ ID NO 10
<211> LENGTH: 340
<212> TYPE: DNA
<213> ORGANISM: Artificial Sequence
<220> FEATURE:
<223> OTHER INFORMATION: Human beta-globin intron

<400> SEQUENCE: 10

```
tacacatatt gaccaaatca gggtaatttt gcatttgtaa ttttaaaaaa tgctttcttc    60
ttttaatata ctttttttgtt tatcttattt ctaatacttt ccctaatctc tttcttcag   120 ggcaataatg atacaatgta tcatgcctct ttgcaccatt ctaaagaata acagtgataa   180
tttctgggtt aaggcaatag caatatttct gcatataaat atttctgcat ataaattgta   240
actgatgtaa gaggtttcat attgctaata gcagctacaa tccagctacc attctgcttt   300 tatttttatgg ttgggataag gctggattat tctgagtcca                        340
```

<210> SEQ ID NO 11
<211> LENGTH: 234
<212> TYPE: DNA
<213> ORGANISM: Artificial Sequence
<220> FEATURE:
<223> OTHER INFORMATION: RRE(Rev response element) : NL4-3 strain

<400> SEQUENCE: 11

```
aggagctttg ttccttgggt tcttgggagc agcaggaagc actatgggcg cagcgtcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcct         234
```

<210> SEQ ID NO 12
<211> LENGTH: 592
<212> TYPE: DNA
<213> ORGANISM: Artificial Sequence
<220> FEATURE:
<223> OTHER INFORMATION: Woodchuck hepatitis B virus (WPRE region)

<400> SEQUENCE: 12

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg gctcggctg    360 ttgggcactg acaattccgt ggtgttgtcg gggaagctga cgtccttttcc atggctgctc   420 gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592
```

<210> SEQ ID NO 13
<211> LENGTH: 193

<212> TYPE: DNA
<213> ORGANISM: Artificial Sequence
<220> FEATURE:
<223> OTHER INFORMATION: Codon-optimized HIV NC for cloning

<400> SEQUENCE: 13

```
aagcttcccg ggaatgcagc ggggaaactt caggaaccag cgaaaaactg tgaagtgctt      60
caattgcgga aaggagggcc acatcgctaa gaactgccgg gcccccagaa agaaaggctg     120
ctggagatgc ggcagagagg gccaccagat gaaggactgc actgagcggc aggcaaactg     180
actgcaggaa ttc                                                        193
```